United States Patent
De Veylder et al.

(10) Patent No.: US 11,193,136 B2
(45) Date of Patent: Dec. 7, 2021

(54) CELLULOSE SYNTHASE INHIBITORS AND MUTANT PLANTS

(71) Applicants: VIB VZW, Ghent (BE); UNIVERSITEIT GENT, Ghent (BE)

(72) Inventors: Lieven De Veylder, Drongen (BE); Rudy Vanderhaeghen, Merelbeke (BE); Zhubing Hu, Ghent (BE)

(73) Assignees: VIB VZW, Ghent (BE); UniversiteitGent, Ghent (BE)

( * ) Notice: Subject to any disclaimer, the term of this patent is extended or adjusted under 35 U.S.C. 154(b) by 134 days.

(21) Appl. No.: 16/323,707

(22) PCT Filed: Aug. 1, 2017

(86) PCT No.: PCT/EP2017/069386
§ 371 (c)(1),
(2) Date: Feb. 6, 2019

(87) PCT Pub. No.: WO2018/029034
PCT Pub. Date: Feb. 15, 2018

(65) Prior Publication Data
US 2019/0177743 A1 Jun. 13, 2019

(30) Foreign Application Priority Data
Aug. 9, 2016 (EP) ..................... 16183333

(51) Int. Cl.
*C12N 15/82* (2006.01)
*C12N 9/10* (2006.01)
*A01N 43/90* (2006.01)

(52) U.S. Cl.
CPC ......... *C12N 15/8274* (2013.01); *A01N 43/90* (2013.01); *C12N 9/1059* (2013.01)

(58) Field of Classification Search
None
See application file for complete search history.

(56) References Cited

FOREIGN PATENT DOCUMENTS

| WO | 2013142968 A1 | 10/2013 | |
|---|---|---|---|
| WO | WO-2013142968 A1 * | 10/2013 | ............. A01N 37/30 |
| WO | 2015162143 A1 | 10/2015 | |
| WO | WO-2015162143 A1 * | 10/2015 | ..... C12Y 204/01012 |

OTHER PUBLICATIONS

Mizuki et al.(J Exp. Bot., 67:533-542, Jan. 2016).*
Harris et al. (PNAS, 109-4098-4103, 2012).*
PCT International Search Report and Written Opinion, Application No. PCT/EP2017/069386, dated Oct. 20, 2017, 10 pages.
Tateno et al., Cellulose Biosynthesis Inhibitors—A Multifunctional Toolbox, Department of Hroticulture, Unviersity of Kentucky, Journal of Experimental Botany, vol. 67, No. 2 pp. 533-542, Nov. 19, 2015, doi:10.1093/jxb/erv489.
Zhubing, Hu, et al., Genome Editing-Based Engineering of CES A3 Dual Cellulose-Inhibitor-Resistant Plants. (Jun. 2019) www.plantphysiol.org vol. 180, pp. 827-836.

* cited by examiner

*Primary Examiner* — Vinod Kumar
(74) *Attorney, Agent, or Firm* — Patent Law Works, LLP

(57) ABSTRACT

The present invention relates to specific inhibitors of the cellulose synthase subunits 1 and 3 activity in plants, useful as a herbicide. In addition, the invention relates to mutant plants which are tolerant to the identified inhibitors. Specific mutant alleles of CESA1 and CESA3 genes can be used to obtain resistance in a plant when the inhibitors are used as herbicide.

Figure 1:
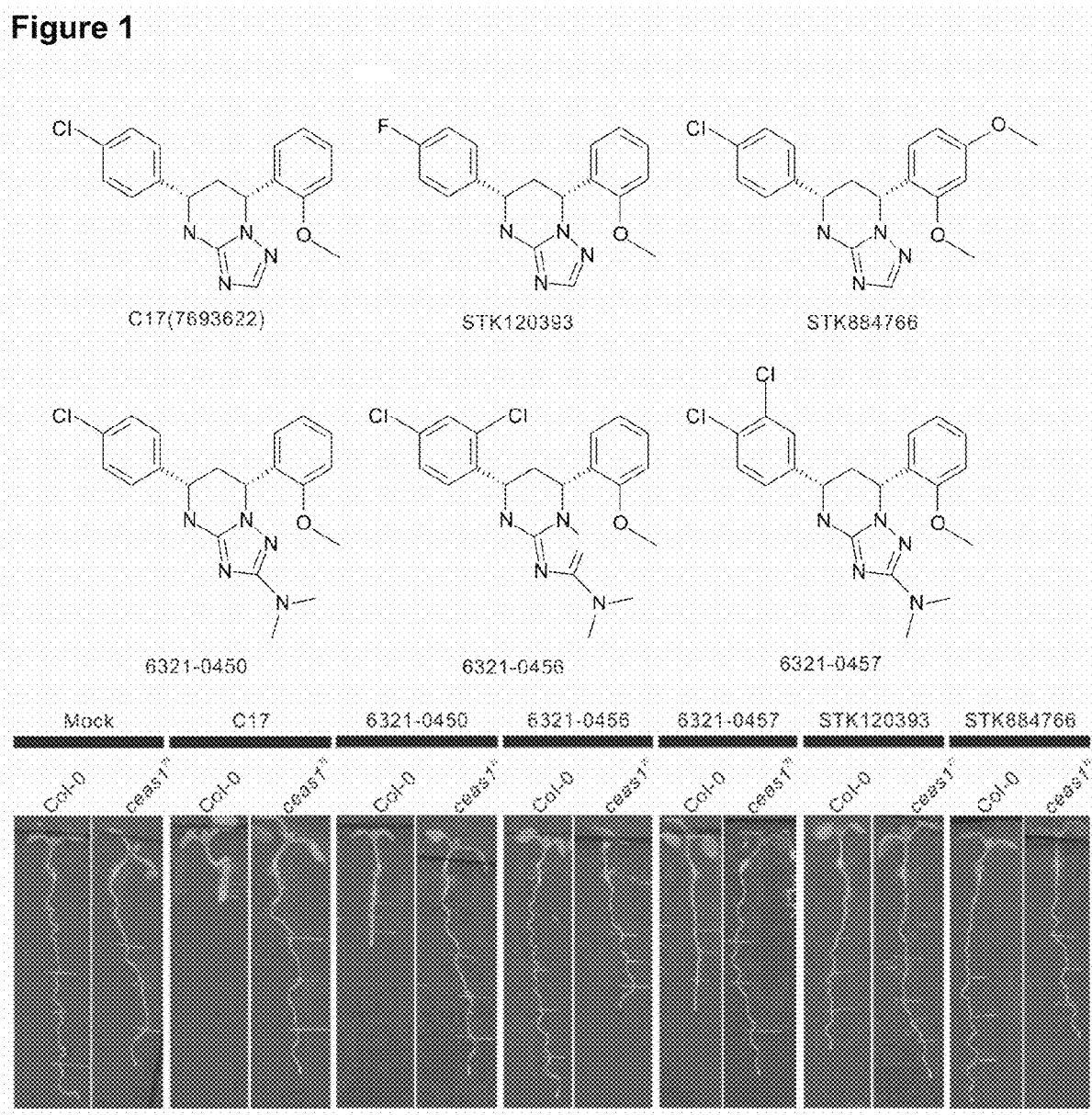

6 Claims, 7 Drawing Sheets
(7 of 7 Drawing Sheet(s) Filed in Color)
Specification includes a Sequence Listing.

SEQUENCE LISTING

<160> NUMBER OF SEQ ID NOS: 16

<210> SEQ ID NO 1
<211> LENGTH: 55
<212> TYPE: DNA
<213> ORGANISM: Artificial Sequence
<220> FEATURE:
<223> OTHER INFORMATION: Primer

<400> SEQUENCE: 1
ggggacaagt ttgtacaaaa aagcaggctt catggaatcc gaaggagaaa ccgcg     55

<210> SEQ ID NO 2
<211> LENGTH: 52
<212> TYPE: DNA
<213> ORGANISM: Artificial Sequence
<220> FEATURE:
<223> OTHER INFORMATION: Primer

<400> SEQUENCE: 2
ggggaccact ttgtacaaga aagctgggtg tcgcttctca acagttgatt cc     52

<210> SEQ ID NO 3
<211> LENGTH: 249
<212> TYPE: PRT
<213> ORGANISM: Arabidopsis thaliana

<400> SEQUENCE: 3

Leu Thr Pro Tyr Arg Val Val Ile Ile Leu Arg Leu Ile Ile Leu Cys
1               5                   10                  15

Phe Phe Leu Gln Tyr Arg Thr Thr His Pro Val Lys Asn Ala Tyr Pro
            20                  25                  30

Leu Trp Leu Thr Ser Val Ile Cys Glu Ile Trp Phe Ala Phe Ser Trp
        35                  40                  45

Leu Leu Ile Thr Ser Ile Pro Leu Ile Ala Tyr Cys Ile Leu Pro Ala
    50                  55                  60

Phe Cys Leu Ile Thr Asp Arg Phe Ile Ile Pro Glu Ile Ser Asn Tyr
65                  70                  75                  80

Ala Ser Ile Trp Phe Ile Leu Leu Phe Ile Ser Ile Ala Val Thr Gly
                85                  90                  95

Ile Leu Glu Leu Arg Trp Ser Gly Val Ser Ile Glu Asp Trp Trp Arg
            100                 105                 110

Asn Glu Gln Phe Trp Val Ile Gly Gly Thr Ser Ala His Leu Phe Ala
        115                 120                 125

Val Phe Gln Gly Leu Leu Lys Val Leu Ala Gly Ile Asp Thr Asn Phe
    130                 135                 140

Thr Val Thr Ser Lys Ala Thr Asp Glu Asp Gly Asp Phe Ala Glu Leu
145                 150                 155                 160

```
Tyr Ile Phe Lys Trp Thr Ala Leu Leu Ile Pro Pro Thr Val Leu
            165                 170                 175

Leu Val Asn Leu Ile Gly Ile Val Ala Gly Val Ser Tyr Ala Val Asn
            180                 185                 190

Ser Gly Tyr Gln Ser Trp Gly Pro Leu Phe Gly Lys Leu Phe Phe Ala
            195                 200                 205

Leu Trp Val Ile Ala His Leu Tyr Pro Phe Leu Lys Gly Leu Leu Gly
            210                 215                 220

Arg Gln Asn Arg Thr Pro Thr Ile Val Ile Val Trp Ser Val Leu Leu
225                 230                 235                 240

Ala Ser Ile Phe Ser Leu Leu Trp Val
            245
```

<210> SEQ ID NO 4
<211> LENGTH: 249
<212> TYPE: PRT
<213> ORGANISM: Glycine max

<400> SEQUENCE: 4

```
Leu Thr Pro Tyr Arg Val Val Ile Ile Leu Arg Leu Ile Ile Leu Gly
1               5                   10                  15

Phe Phe Leu Gln Tyr Arg Val Thr His Pro Val Lys Asp Ala Tyr Pro
            20                  25                  30

Leu Trp Leu Thr Ser Val Ile Cys Glu Ile Trp Phe Ala Leu Ser Trp
            35                  40                  45

Leu Leu Phe Thr Ser Ile Pro Leu Ile Ala Tyr Cys Thr Leu Pro Ala
        50                  55                  60

Phe Cys Leu Leu Thr Asn Lys Phe Ile Ile Pro Glu Ile Ser Asn Phe
65                  70                  75                  80

Ala Ser Met Trp Phe Ile Leu Leu Phe Val Ser Ile Phe Thr Thr Ser
            85                  90                  95

Ile Leu Glu Leu Arg Trp Ser Gly Val Ser Ile Glu Asp Trp Trp Arg
            100                 105                 110

Asn Glu Gln Phe Trp Val Ile Gly Gly Thr Ser Ala His Leu Phe Ala
            115                 120                 125

Val Phe Gln Gly Leu Leu Lys Val Leu Ala Gly Ile Asp Thr Asn Phe
            130                 135                 140

Thr Val Thr Ser Lys Ala Ser Asp Glu Asp Gly Asp Phe Ala Glu Leu
145                 150                 155                 160

Tyr Val Phe Lys Trp Thr Ser Leu Leu Ile Pro Pro Thr Thr Val Leu
            165                 170                 175

Ile Val Asn Leu Val Gly Ile Val Ala Gly Val Ser Tyr Ala Ile Asn
            180                 185                 190

Ser Gly Tyr Gln Ser Trp Gly Pro Leu Phe Gly Lys Leu Phe Phe Ala
            195                 200                 205

Ile Trp Val Ile Ala His Leu Tyr Pro Phe Leu Lys Gly Leu Leu Gly
            210                 215                 220

Arg Gln Asn Arg Thr Pro Thr Ile Val Ile Val Trp Ser Val Leu Leu
225                 230                 235                 240

Ala Ser Ile Phe Ser Leu Leu Trp Val
            245
```

<210> SEQ ID NO 5
<211> LENGTH: 249
<212> TYPE: PRT

<213> ORGANISM: Fragaria vesca

<400> SEQUENCE: 5

Leu Thr Pro Tyr Arg Val Val Ile Ile Leu Arg Leu Ile Ile Leu Cys
1               5                   10                  15

Phe Phe Leu Gln Tyr Arg Ala Thr His Pro Val Lys Asp Ala Tyr Pro
            20                  25                  30

Leu Trp Leu Ile Ser Val Ile Cys Glu Ile Trp Phe Ala Phe Ser Trp
        35                  40                  45

Leu Leu Leu Thr Ser Ile Pro Leu Ile Ala Tyr Cys Met Leu Pro Ala
50                  55                  60

Phe Cys Leu Leu Thr Asn Lys Phe Ile Ile Pro Glu Ile Ser Asn Phe
65                  70                  75                  80

Ala Ser Met Trp Phe Ile Leu Leu Phe Val Ser Ile Ala Ala Thr Gly
                85                  90                  95

Ile Leu Glu Leu Arg Trp Ser Gly Val Gly Ile Asp Asp Trp Trp Arg
            100                 105                 110

Asn Glu Gln Phe Trp Val Ile Gly Gly Thr Ser Ala His Leu Phe Ala
        115                 120                 125

Val Phe Gln Gly Leu Leu Lys Val Leu Ala Gly Ile Asp Thr Asn Phe
130                 135                 140

Thr Val Thr Ser Lys Ala Ser Asp Glu Asp Gly Asp Phe Ala Glu Leu
145                 150                 155                 160

Tyr Val Phe Lys Trp Thr Ser Leu Leu Ile Pro Pro Thr Thr Val Leu
                165                 170                 175

Ile Val Asn Leu Val Gly Ile Val Ala Gly Val Ser Tyr Ala Ile Asn
            180                 185                 190

Ser Gly Tyr Gln Ser Trp Gly Pro Leu Phe Gly Lys Leu Phe Phe Ala
        195                 200                 205

Met Trp Val Val Ala His Leu Tyr Pro Phe Leu Lys Gly Leu Leu Gly
210                 215                 220

Arg Gln Asn Arg Thr Pro Thr Ile Val Ile Val Trp Ser Ile Leu Leu
225                 230                 235                 240

Ala Ser Ile Phe Ser Leu Leu Trp Val
                245

<210> SEQ ID NO 6
<211> LENGTH: 249
<212> TYPE: PRT
<213> ORGANISM: Vitis vinifera

<400> SEQUENCE: 6

Leu Thr Pro Tyr Arg Val Val Ile Ile Leu Arg Leu Ile Ile Leu Gly
1               5                   10                  15

Phe Phe Leu Gln Tyr Arg Thr Thr His Pro Val Lys Asp Ala Tyr Pro
            20                  25                  30

Leu Trp Leu Thr Ser Val Ile Cys Glu Ile Trp Phe Ala Leu Ser Trp
        35                  40                  45

Leu Leu Leu Thr Ser Ile Pro Leu Ile Ala Tyr Cys Val Leu Pro Ala
50                  55                  60

Ile Cys Leu Leu Thr Gly Lys Phe Ile Ile Pro Glu Ile Ser Asn Phe
65                  70                  75                  80

Ala Ser Met Trp Phe Ile Leu Leu Phe Val Ser Ile Phe Ala Thr Gly
                85                  90                  95

Ile Leu Glu Leu Arg Trp Ser Gly Val Ser Ile Glu Asp Trp Trp Arg

```
                    100                 105                 110
Asn Glu Gln Phe Trp Val Ile Gly Gly Thr Ser Ala His Leu Phe Ala
            115                 120                 125

Val Phe Gln Gly Leu Leu Lys Val Leu Ala Gly Ile Asp Thr Asn Phe
        130                 135                 140

Thr Val Thr Ser Lys Ala Ser Asp Asp Gly Asp Phe Ala Glu Leu
145                 150                 155                 160

Tyr Val Phe Lys Trp Thr Ser Leu Leu Ile Pro Pro Thr Thr Val Leu
                165                 170                 175

Val Val Asn Leu Val Gly Ile Val Ala Gly Val Ser Tyr Ala Ile Asn
            180                 185                 190

Ser Gly Tyr Gln Ser Trp Gly Pro Leu Phe Gly Lys Leu Phe Phe Ala
        195                 200                 205

Ile Trp Val Ile Val His Leu Tyr Pro Phe Leu Lys Gly Leu Leu Gly
    210                 215                 220

Arg Gln Asn Arg Thr Pro Thr Ile Val Ile Val Trp Ser Ile Leu Leu
225                 230                 235                 240

Ala Ser Ile Phe Ser Leu Leu Trp Val
                245

<210> SEQ ID NO 7
<211> LENGTH: 249
<212> TYPE: PRT
<213> ORGANISM: Solanum lycopersicum

<400> SEQUENCE: 7

Leu Thr Pro Tyr Arg Val Ile Ile Leu Arg Leu Ile Ile Leu Gly
1               5                   10                  15

Phe Phe Met Gln Tyr Arg Leu Thr His Pro Val Asn Asp Ala Tyr Pro
                20                  25                  30

Leu Trp Leu Val Ser Val Ile Cys Glu Val Trp Phe Ala Leu Ser Trp
            35                  40                  45

Leu Leu Leu Thr Ser Leu Pro Leu Leu Ala Tyr Cys Thr Leu Pro Ala
        50                  55                  60

Ile Cys Leu Leu Thr Gly Lys Phe Ile Ile Pro Glu Ile Ser Asn Tyr
65                  70                  75                  80

Ala Gly Met Trp Phe Ile Leu Leu Phe Leu Ser Ile Phe Ala Thr Gly
                85                  90                  95

Ile Leu Glu Leu Arg Trp Ser Gly Val Ser Ile Glu Asp Trp Trp Arg
            100                 105                 110

Asn Glu Gln Phe Trp Val Ile Gly Gly Thr Ser Ala His Leu Phe Ala
        115                 120                 125

Val Phe Gln Gly Leu Leu Lys Val Leu Ala Gly Ile Asp Thr Asn Phe
    130                 135                 140

Thr Val Thr Ser Lys Ala Asn Asp Glu Asp Gly Asp Phe Ala Glu Leu
145                 150                 155                 160

Tyr Val Phe Lys Trp Thr Thr Leu Leu Ile Pro Pro Thr Ala Ile Leu
                165                 170                 175

Ile Val Asn Leu Val Gly Ile Val Ala Gly Val Ser Tyr Ala Ile Asn
            180                 185                 190

Ser Gly Tyr Gln Ser Trp Gly Pro Leu Phe Gly Lys Leu Phe Phe Ala
        195                 200                 205

Ile Trp Val Ile Val His Leu Tyr Pro Phe Leu Lys Gly Leu Leu Gly
    210                 215                 220
```

Arg Gln Asn Arg Thr Pro Thr Ile Val Ile Val Trp Ala Val Leu Leu
225                 230                 235                 240

Ala Ser Ile Phe Ser Leu Leu Trp Val
                245

<210> SEQ ID NO 8
<211> LENGTH: 249
<212> TYPE: PRT
<213> ORGANISM: Zea mays

<400> SEQUENCE: 8

Leu Asn Leu Tyr Arg Val Val Ile Ile Leu Arg Leu Ile Ile Leu Cys
1               5                   10                  15

Phe Phe Phe Gln Tyr Arg Val Ser His Pro Val Arg Asp Ala Tyr Gly
                20                  25                  30

Leu Trp Leu Val Ser Val Ile Cys Glu Val Trp Phe Ala Leu Ser Trp
            35                  40                  45

Leu Leu Ile Thr Ser Ile Pro Leu Ile Ala Tyr Cys Val Leu Pro Ala
        50                  55                  60

Ile Cys Leu Leu Thr Asn Lys Phe Ile Ile Pro Glu Ile Ser Asn Tyr
65                  70                  75                  80

Ala Gly Met Phe Phe Ile Leu Leu Phe Ala Ser Ile Phe Ala Thr Gly
                85                  90                  95

Ile Leu Glu Leu Arg Trp Ser Gly Val Gly Ile Glu Asp Trp Trp Arg
                100                 105                 110

Asn Glu Gln Phe Trp Val Ile Gly Gly Thr Ser Ala His Leu Phe Ala
                115                 120                 125

Val Phe Gln Gly Leu Leu Lys Val Leu Ala Gly Ile Asp Thr Asn Phe
        130                 135                 140

Thr Val Thr Ser Lys Ala Ser Asp Glu Asp Gly Asp Phe Ala Glu Leu
145                 150                 155                 160

Tyr Val Phe Lys Trp Thr Ser Leu Leu Ile Pro Pro Thr Thr Val Leu
                165                 170                 175

Val Ile Asn Leu Val Gly Met Val Ala Gly Ile Ser Tyr Ala Ile Asn
                180                 185                 190

Ser Gly Tyr Gln Ser Trp Gly Pro Leu Phe Gly Lys Leu Phe Phe Ser
            195                 200                 205

Ile Trp Val Ile Leu His Leu Tyr Pro Phe Leu Lys Gly Leu Met Gly
210                 215                 220

Arg Gln Asn Arg Thr Pro Thr Ile Val Ile Val Trp Ser Ile Leu Leu
225                 230                 235                 240

Ala Ser Ile Phe Ser Leu Leu Trp Val
                245

<210> SEQ ID NO 9
<211> LENGTH: 249
<212> TYPE: PRT
<213> ORGANISM: Oryza sativa

<400> SEQUENCE: 9

Leu Asn Leu Tyr Arg Ile Val Ile Ile Leu Arg Leu Ile Ile Leu Met
1               5                   10                  15

Phe Phe Phe Gln Tyr Arg Val Thr His Pro Val Arg Asp Ala Tyr Gly
                20                  25                  30

Leu Trp Leu Val Ser Val Ile Cys Glu Ile Trp Phe Ala Leu Ser Trp
            35                  40                  45

```
Leu Leu Ile Thr Ser Ile Pro Leu Ile Ala Tyr Cys Val Leu Pro Ala
 50                  55                  60

Ile Cys Leu Leu Thr Asn Lys Phe Ile Pro Glu Ile Ser Asn Tyr
 65                  70                  75                  80

Ala Gly Met Phe Phe Ile Leu Leu Phe Ala Ser Ile Phe Ala Thr Gly
                 85                  90                  95

Ile Leu Glu Leu Arg Trp Ser Gly Val Gly Ile Glu Asp Trp Trp Arg
                100                 105                 110

Asn Glu Gln Phe Trp Val Ile Gly Gly Thr Ser Ala His Leu Phe Ala
                115                 120                 125

Val Phe Gln Gly Leu Leu Lys Val Leu Ala Gly Ile Asp Thr Asn Phe
        130                 135                 140

Thr Val Thr Ser Lys Ala Ser Asp Glu Asp Gly Asp Phe Ala Glu Leu
145                 150                 155                 160

Tyr Val Phe Lys Trp Thr Ser Leu Leu Ile Pro Pro Thr Thr Val Leu
                165                 170                 175

Val Ile Asn Leu Val Gly Met Val Ala Gly Ile Ser Tyr Ala Ile Asn
                180                 185                 190

Ser Gly Tyr Gln Ser Trp Gly Pro Leu Phe Gly Lys Leu Phe Phe Ser
        195                 200                 205

Ile Trp Val Ile Leu His Leu Tyr Pro Phe Leu Lys Gly Leu Met Gly
210                 215                 220

Arg Gln Asn Arg Thr Pro Thr Ile Val Ile Val Trp Ser Ile Leu Leu
225                 230                 235                 240

Ala Ser Ile Phe Ser Leu Leu Trp Val
                245

<210> SEQ ID NO 10
<211> LENGTH: 85
<212> TYPE: PRT
<213> ORGANISM: Arabidopsis thaliana

<400> SEQUENCE: 10

Trp Thr Thr Leu Leu Ile Pro Pro Thr Thr Leu Leu Ile Val Asn Leu
1               5                   10                  15

Val Gly Val Val Ala Gly Val Ser Tyr Ala Ile Asn Ser Gly Tyr Gln
                20                  25                  30

Ser Trp Gly Pro Leu Phe Gly Lys Leu Phe Phe Ala Phe Trp Val Ile
            35                  40                  45

Val His Leu Tyr Pro Phe Leu Lys Gly Leu Met Gly Arg Gln Asn Arg
        50                  55                  60

Thr Pro Thr Ile Val Val Val Trp Ser Val Leu Leu Ala Ser Ile Phe
65                  70                  75                  80

Ser Leu Leu Trp Val
                85

<210> SEQ ID NO 11
<211> LENGTH: 85
<212> TYPE: PRT
<213> ORGANISM: Glycine max

<400> SEQUENCE: 11

Trp Thr Thr Leu Leu Ile Pro Pro Thr Thr Leu Leu Ile Ile Asn Leu
1               5                   10                  15

Val Gly Val Val Ala Gly Ile Ser Tyr Ala Ile Asn Ser Gly Tyr Gln
                20                  25                  30
```

Ser Trp Gly Pro Leu Phe Gly Lys Leu Phe Phe Ala Phe Trp Val Ile
            35                  40                  45

Ile His Leu Tyr Pro Phe Leu Lys Gly Leu Met Gly Arg Gln Asn Arg
    50                  55                  60

Thr Pro Thr Ile Val Val Val Trp Ser Val Leu Leu Ala Ser Ile Phe
65                  70                  75                  80

Ser Leu Leu Trp Val
                85

<210> SEQ ID NO 12
<211> LENGTH: 85
<212> TYPE: PRT
<213> ORGANISM: Fragaria vesca

<400> SEQUENCE: 12

Trp Thr Thr Leu Leu Ile Pro Pro Thr Thr Leu Leu Ile Ile Asn Leu
1               5                   10                  15

Val Gly Val Val Ala Gly Ile Ser Tyr Ala Val Asn Ser Gly Tyr Gln
            20                  25                  30

Ser Trp Gly Pro Leu Phe Gly Lys Leu Phe Phe Ala Phe Trp Val Ile
            35                  40                  45

Val His Leu Tyr Pro Phe Leu Lys Gly Leu Met Gly Arg Gln Asn Arg
    50                  55                  60

Thr Pro Thr Ile Val Val Val Trp Ser Val Leu Leu Ala Ser Ile Phe
65                  70                  75                  80

Ser Leu Leu Trp Val
                85

<210> SEQ ID NO 13
<211> LENGTH: 85
<212> TYPE: PRT
<213> ORGANISM: Vitis vinifera

<400> SEQUENCE: 13

Trp Thr Thr Leu Leu Ile Pro Pro Thr Thr Leu Leu Ile Ile Asn Leu
1               5                   10                  15

Val Gly Val Val Ala Gly Ile Ser Tyr Ala Ile Asn Ser Gly Tyr Gln
            20                  25                  30

Ser Trp Gly Pro Leu Phe Gly Lys Leu Phe Phe Ala Phe Trp Val Ile
            35                  40                  45

Val His Leu Tyr Pro Phe Leu Lys Gly Leu Met Gly Arg Gln Asn Arg
    50                  55                  60

Thr Pro Thr Ile Val Val Trp Ser Ile Leu Leu Ala Ser Ile Phe
65                  70                  75                  80

Ser Leu Leu Trp Val
                85

<210> SEQ ID NO 14
<211> LENGTH: 85
<212> TYPE: PRT
<213> ORGANISM: Solanum lycopersicum

<400> SEQUENCE: 14

Trp Thr Thr Leu Leu Ile Pro Pro Thr Thr Leu Leu Ile Val Asn Leu
1               5                   10                  15

Val Gly Val Val Ala Gly Ile Ser Tyr Ala Val Asn Ser Gly Tyr Gln
            20                  25                  30

Ser Trp Gly Pro Leu Phe Gly Lys Leu Phe Phe Ala Phe Trp Val Ile

```
                    35                  40                  45
Val His Leu Tyr Pro Phe Leu Lys Gly Leu Met Gly Arg Gln Asn Arg
    50                  55                  60

Thr Pro Thr Ile Val Val Trp Ser Ile Leu Leu Ala Ser Ile Phe
65                  70                  75                  80

Ser Leu Leu Trp Val
                85

<210> SEQ ID NO 15
<211> LENGTH: 85
<212> TYPE: PRT
<213> ORGANISM: Zea mays

<400> SEQUENCE: 15

Trp Thr Thr Leu Leu Ile Pro Pro Thr Thr Val Leu Val Ile Asn Leu
1               5                  10                  15

Val Gly Ile Val Ala Gly Val Ser Tyr Ala Ile Asn Ser Gly Tyr Gln
                20                  25                  30

Ser Trp Gly Pro Leu Phe Gly Lys Leu Phe Ala Ile Trp Val Ile
        35                  40                  45

Leu His Leu Tyr Pro Phe Leu Lys Gly Leu Met Gly Lys Gln Asn Arg
    50                  55                  60

Thr Pro Thr Ile Val Ile Val Trp Ser Val Leu Leu Ala Ser Ile Phe
65                  70                  75                  80

Ser Leu Leu Trp Val
                85

<210> SEQ ID NO 16
<211> LENGTH: 85
<212> TYPE: PRT
<213> ORGANISM: Oryza sativa

<400> SEQUENCE: 16

Trp Thr Thr Leu Leu Ile Pro Pro Thr Thr Ile Leu Ile Ile Asn Leu
1               5                  10                  15

Val Gly Val Val Ala Gly Ile Ser Tyr Ala Ile Asn Ser Gly Tyr Gln
                20                  25                  30

Ser Trp Gly Pro Leu Phe Gly Lys Leu Phe Phe Ala Phe Trp Val Ile
        35                  40                  45

Val His Leu Tyr Pro Phe Leu Lys Gly Leu Met Gly Arg Gln Asn Arg
    50                  55                  60

Thr Pro Thr Ile Val Val Val Trp Ala Ile Leu Leu Ala Ser Ile Phe
65                  70                  75                  80

Ser Leu Leu Trp Val
                85
```

CELLULOSE SYNTHASE INHIBITORS AND MUTANT PLANTS

FIELD OF THE INVENTION

The present invention relates to specific inhibitors of the cellulose synthase subunits 1 and 3 activity in plants, useful as a herbicide. In addition, the invention relates to mutant plants which are tolerant to the identified inhibitors. Specific mutant alleles of CESA1 and CESA3 genes can be used to obtain resistance in a plant when the inhibitors are used as herbicide.

INTRODUCTION TO THE INVENTION

Plant cells walls are essential for the plant rigidity and strength, but they protect the plant also against environmental stress. Cellulose is one of the major compounds of the plant cell wall. Cellulose is a hydrogen bonded beta-1,4-linked glucan microfibril, and is synthesized by large multimeric cellulose synthase complexes (CSC). The CSCs can be divided in a primary cell wall CSC and a secondary cell wall CSC (Endler and Person, 2011). The CSC is a large, hexameric rosette like structure, comprising six globular protein complexes (Kimura et al., 1999). Each of those complexes is holding 6 cellulose synthase subunits (CESAs); the CESAs are believed to be the catalytic subunits of the complex. At least three different CESAs are present in a complex (Festucci-Buselli et al., 2007; Lei et al., 2012); the CSC of the primary cell wall synthesis is composed of CESA 1, 3 and 6 (or 6-like proteins CESA2,5 and 9), the CSC of the secondary cell wall synthesis is composed of CESA 4, 7 and 8 (Lei et al., 2012).

Due to the important role of cellulose in plant structure at one hand, and the fact cellulose is a plant specific compound, cellulose synthase is an interesting target for herbicides, as cellulose synthase inhibitors are expected to be efficient in herbicidal activity without major negative effects on animal life forms. Several cellulose biosynthesis inhibitors, such as dichlobenil, isoxaben, quinoxyphen and flupoxam have indeed been developed as herbicides. The mode of action of those herbicides has been studied, and the four herbicides work at a different level (Brabham and DeBolt, 2013). Mutations that confer resistance to isoxaben have been identified in CESA3 and CESA6 (Heim et al., 1989, Scheible et al., 2001, Deprez et al., 2002). However, those mutations cannot rescue the toxicity of dichlobenil. Apparently, dichobenil acts at the level of secondary cell wall synthesis (Brabham and DeBolt, 2013). Quinoxyphen is also working at the level of primary cell wall synthesis, but the resistance is mapping in CESA1 (Harris et al., 2012), Flupoxam is inhibiting cellulose biosynthesis, and hypersensitive mutants have been isolated (Austin et al., 2011), but its mode of action is still unknown (Garcia-Angulo, et al., 2012).

Surprisingly, we found a new group of compounds that can be used as inhibitors of the cellulose biosynthesis. Even more surprisingly, those compounds are acting be a new mechanisms, as the can be rescued by specific mutations in CESA 1, as well as in CESA 3. They differ in this respect from all the known cellulose inhibitors, and their resistance genes. The new class of compounds is useful as herbicides, the combination of compounds and resistance gene can be used as a transformation marker system, or it may be used in agriculture for the generation of herbicide resistant plants comprising one or more alleles of the identified mutants in CESA1 and/or CESA3.

FIGURES

The patent or application file contains at least one drawing executed in color Copies of this patent or patent application publication with color drawing(s) will be provided by the Office upon request and payment of the necessary fee.

FIG. 1: Structure of the different herbicide variants, and their effect on the growth of wild type *Arabidopsis* (Col-0) and a resistant mutant CESA1$^{A1018V}$ (indicated as cesa1$^{7I}$).

Figure 2:
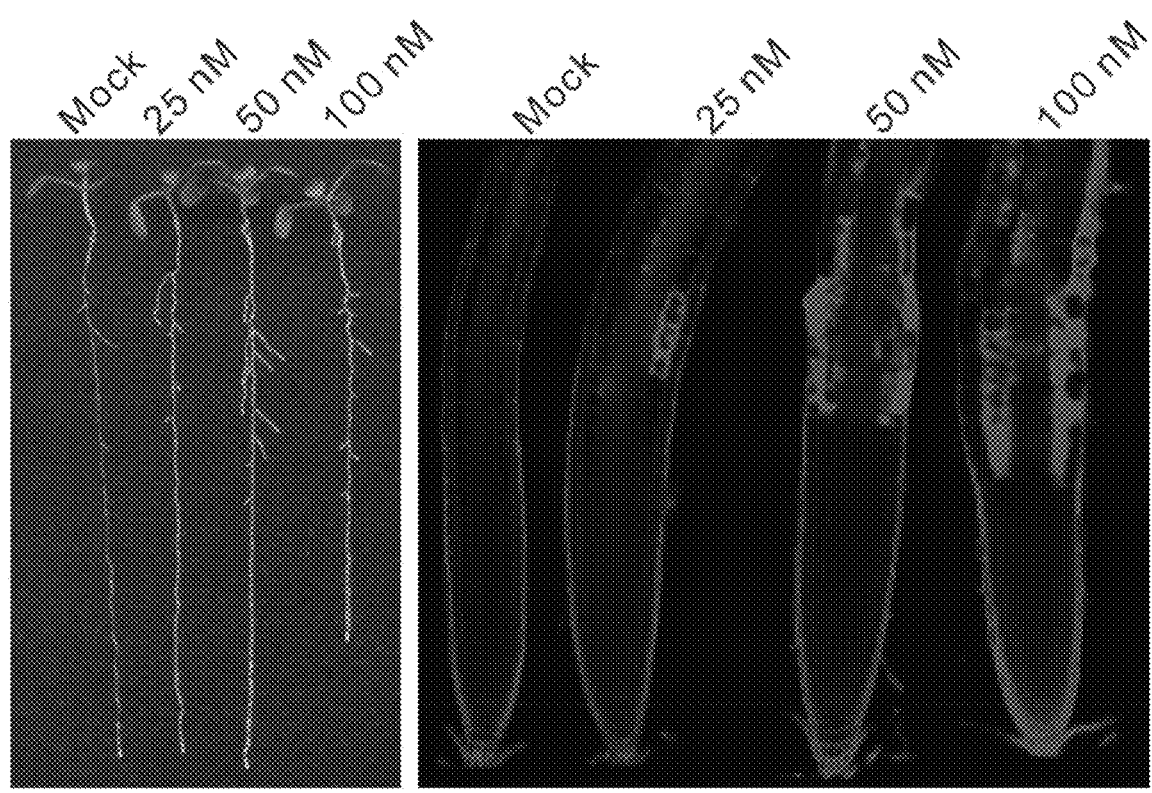

FIG. 2: Left panel: inhibitory effect on root growth of the compound C17(7693622) at different concentrations. Right panel: analysis of cell death in the root of —*Arabidopsis*, caused by increasing concentrations of the compound C17 (7693622).

Figure 3:
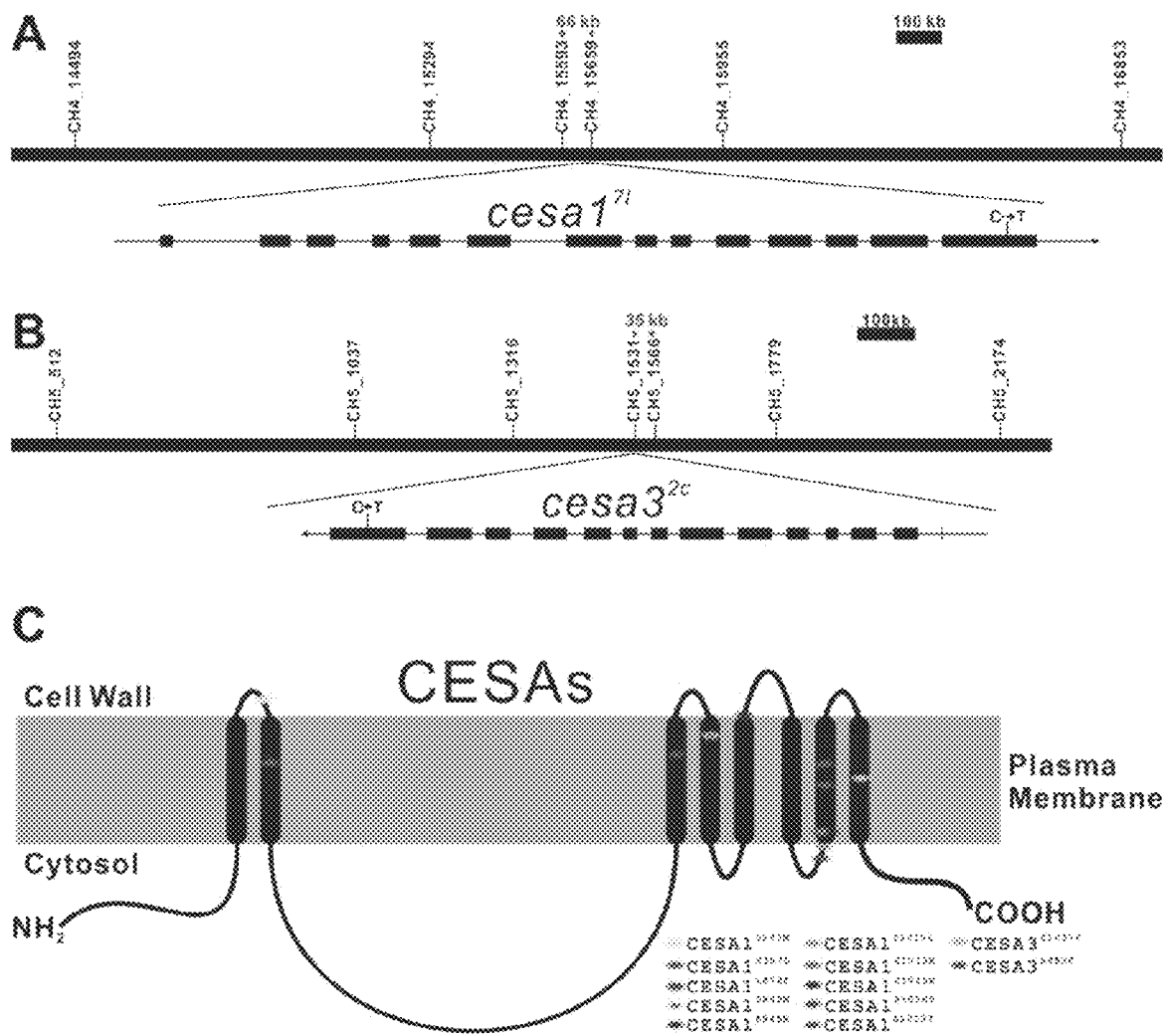

FIG. 3: Identification of mutants, resistant against compound C17(7693622). A. Fine mapping of the mutation cesa1$^{7I}$ (=CESA1$^{A1080V}$) identified in CESA1. B. Fine mapping of the mutation cesa3$^{2c}$ (=CESA3$^{S983F}$) identified in CESA3. C. Mapping of all the mutations identified on the transmembranary structure of CESAs.

Figure 4:
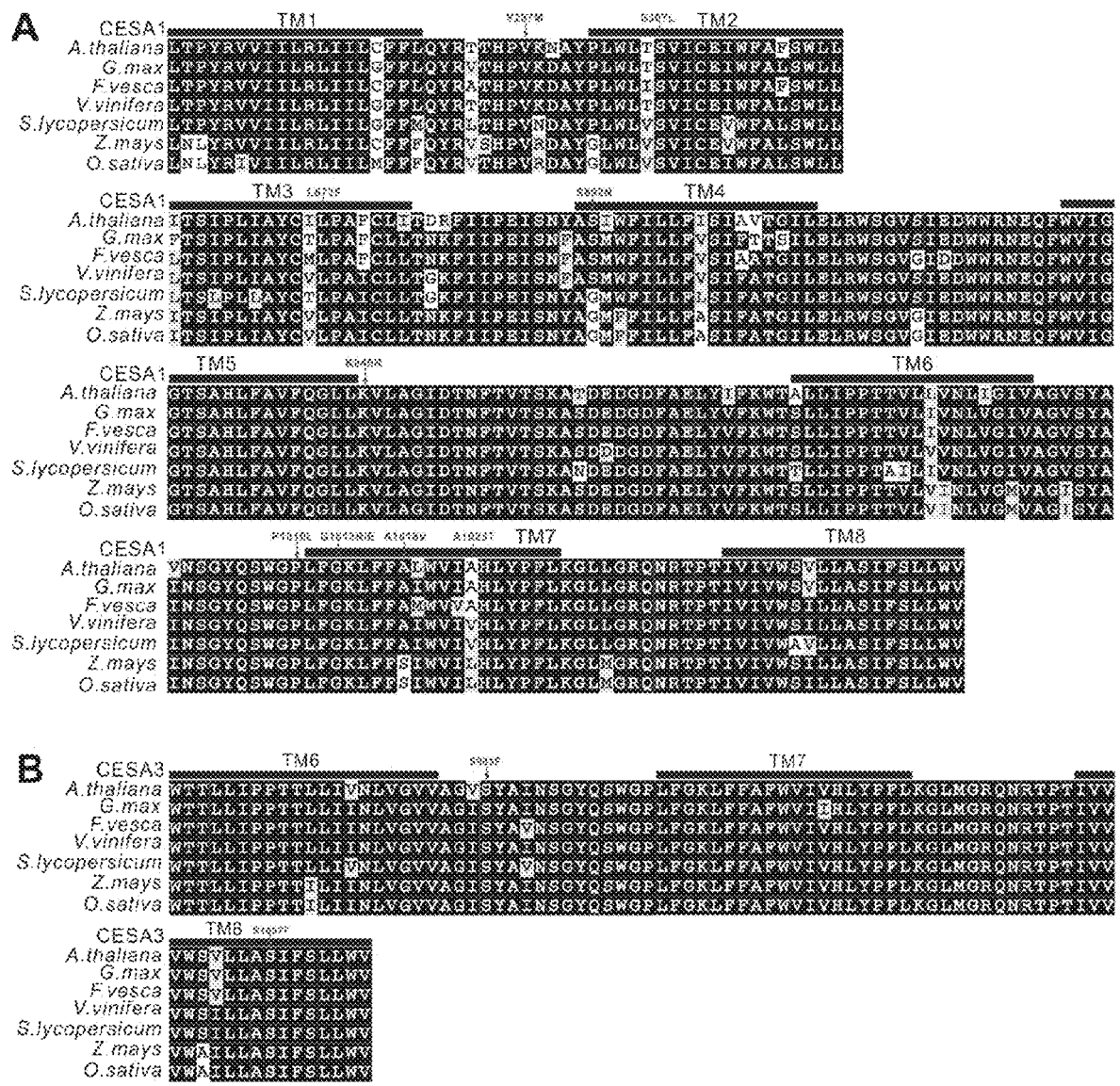

FIG. 4: Sequence alignment of CESA (A) (*A.thaliana* (SEQ ID NO:3); *G.max* (SEQ ID NO:4); *F.vesca* (SEQ ID NO:5); *V.vinifera* (SEQ ID NO:6); *S.lycopersicum* (SEQ ID NO:7); *Z.mays* (SEQ ID NO:8); and *O.sativa* (SEQ ID NO:9)); and CESA3 (B) (*A.thaliana* (SEQ ID NO:10); *G.max* (SEQ ID NO:11); *F.vesca* (SEQ ID NO:12); *V.vinifera* (SEQ ID NO:13); *S.lycopersicum* (SEQ ID NO:14); *Z.mays* (SEQ ID NO:15); and *O.sativa* (SEQ ID NO:16)). Sequences were aligned with a multiple sequence alignment programme (world wide web at genome.jp/tools/clustalw/) using CLUSTALW algorithms. Protein database accession numbers are: CESA1*A.thaliana*-NP_194967; CESA1*G.max*-XP_003522623; CESA1*F.vesca*-XP_004291468; CESA1*V.vinifera*-XP_002282575; CESA1*S.lycopersicum*-XP_004245031; CESA1*Z.mays*-NP_001104954; CESA1*O.sativa*-NP_001054788; CESA3*A.thaliana*-NP_196136; CESA3*G.max*-XP_003540527; CESA3*F.vesca*-XP_004306536; CESA3*V.vinifera*-XP_002278997; CESA3*S.lycopersicum*-XP_004229630; CESA3*Z.mays*-NP_001105621; CESA3*O.sativa*-NP_001059162. The amino acid regions harbouring amino acid replacements in C17-tolerant mutants were selected. Arrowheads indicate the positions of the mutated amino acids. The dark lines indicate the predicted transmembrane domains (TM1 to TM8).

Figure 5:
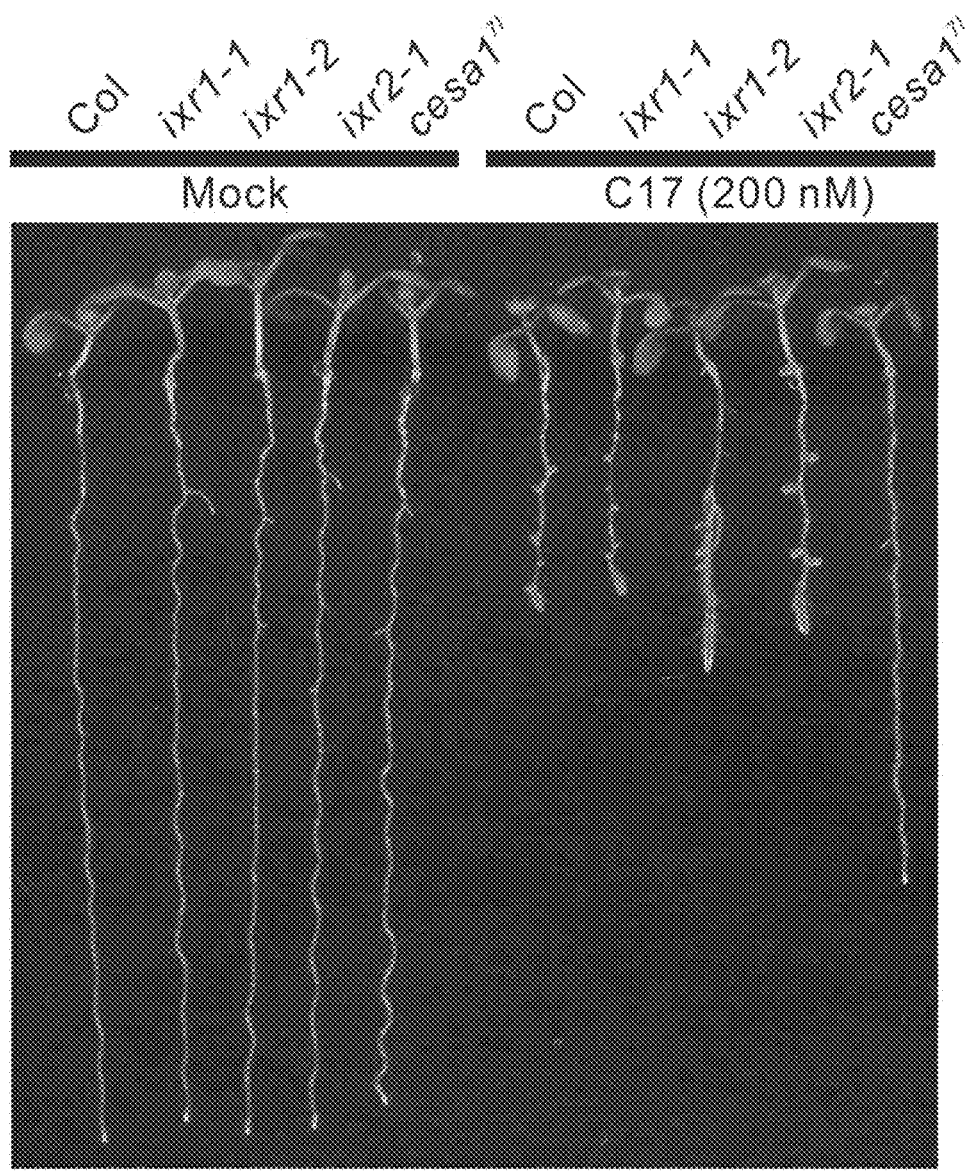

FIG. 5: Sensitivity of Isoxaben resistant mutants to the compound C17(7693622), proving the different working mechanism of compound C17(7693622).

Figure 6:
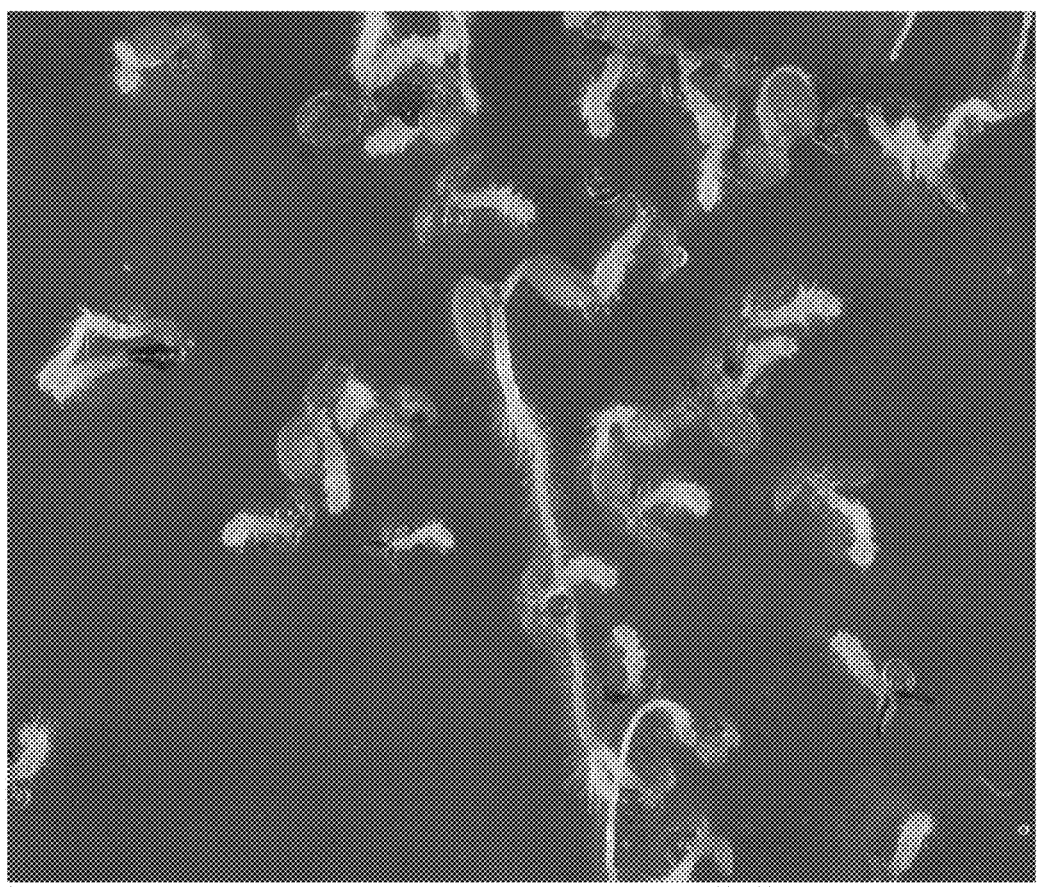

FIG. 6: Use of the combination of compound C17 (7693622) as inhibiting compound and the CESA3 resistance gene as transformation marker: plants carrying the resistant gene can easily be distinguished from the non-transformed control.

Figure 7:
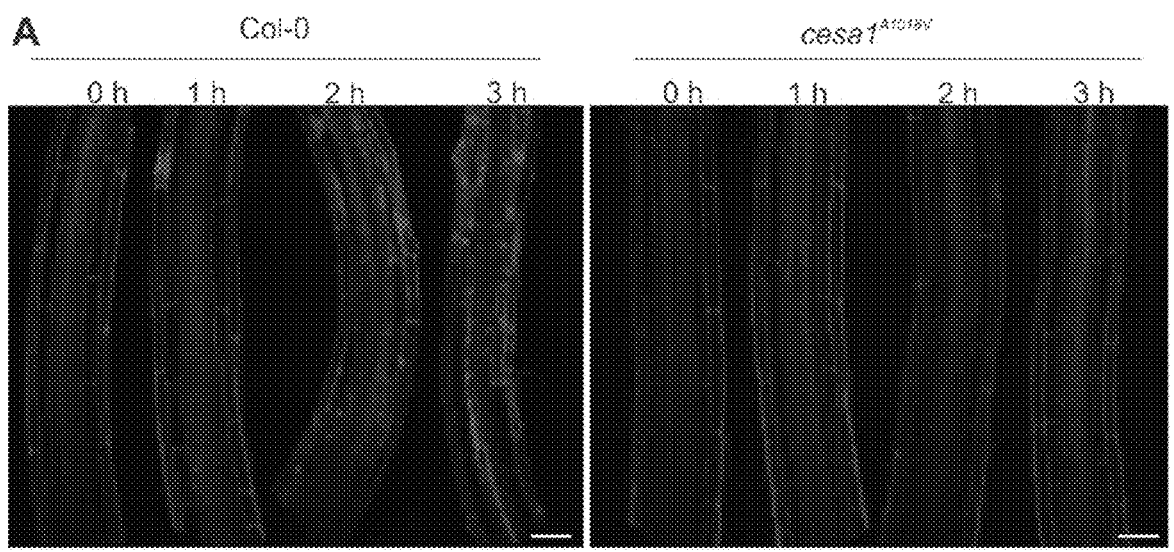

FIG. 7: The application of compound C17 results in a brittle cell wall. (A) Representative confocal microscopy images of plants stained with propidium iodide (PI). Four-day-old wild-type (Col-0, left panel) and C17 tolerant mutant (cesa1A1018V, right panel) seedlings were treated with 200 nM C17 for 0 h, 1 h, 2 h or 3 h and roots were collected and stained with PI. The broken cells with brittle cell wall were visualized by the uptake of PI. Scale bars=50 µm.

DETAILED DESCRIPTION OF THE INVENTION

As used herein, each of the following terms has the meaning associated with it in this section. The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein.

Unless specifically defined herein, all terms used herein have the same meaning as they would to one skilled in the art of the present invention. Practitioners are particularly directed to Sambrook et al., Molecular Cloning: A Laboratory Manual, 4$^{th}$ ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

In a first embodiment the invention provides a mutant CESA1 or mutant CESA3 gene wherein said mutation encodes for a mutant CESA1 or CESA3 protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$ CESA3$^{S983F}$ and CESA3$^{S1037F}$.

In yet another embodiment the invention provides a mutant CESA1 or mutant CESA3 gene wherein said mutation encodes for a mutant CESA1 or CESA3 protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$, CESA1$^{S1018V}$, CESA1$^{A1023T}$ CESA1$^{L1023T}$ and CESA1$^{V1023T}$.

In another embodiment the invention provides a plant having a mutation in the CESA1 or CESA3 gene wherein said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$.

In another embodiment the invention provides a plant having a mutation in the CESA1 or CESA3 gene wherein said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$, CESA1$^{S1018V}$, CESA1$^{A1023T}$, CESA1$^{L1023T}$ and CESA1$^{V1023T}$.

In yet another embodiment the plant has a mutation in at least one CESA1 or CESA3 allele said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$.

In yet another embodiment the plant has a mutation in at least one CESA1 or CESA3 allele said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$ CESA1$^{S1018V}$, CESA1$^{A1023T}$, CESA1$^{L1023T}$ and CESA1$^{V1023T}$.

In yet another embodiment the plant has a mutation in at least two CESA1 or CESA3 alleles said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$.

In yet another embodiment the plant has a mutation in at least two CESA1 or CESA3 alleles said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$, CESA1$^{S1018V}$, CESA1$^{A1023T}$, CESA1$^{L1023T}$ and CESA1$^{V1023T}$.

In yet another embodiment the plant has a mutation in all CESA1 or CESA3 alleles said mutation encodes for a mutant protein selected from the group consisting of CESA1$^{V2971M}$, CESA1$^{S307L}$, CESA1$^{L872F}$, CESA1$^{S892N}$, CESA1$^{G892N}$, CESA1$^{K94512}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$ CESA3$^{S983F}$ and CESA3$^{S1037F}$.

In yet another embodiment the plant has a mutation in all CESA1 or CESA3 alleles said mutation encodes for a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$, CESA1$^{S1018V}$, CESA1$^{A1023T}$, CESA1$^{L1023T}$ and CESA1$^{V1023T}$.

It is well known in the art to introduce specific mutations in plants. Indeed, significant advances have been made in the last few years towards development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide within a predetermined genomic locus. See, for example, U.S. Patent Publication No. 20030232410; 20050208489; 20050026157;

20050064474; and 20060188987, and WO 2007/014275, the disclosures of which are incorporated by reference in their entireties for all purposes. U. 520080182332 describes the use of non-canonical zinc finger nucleases (ZFNs) for targeted modification of plant genomes and U.S. Patent Publication No. 20090205083 describes ZFN-mediated targeted modification of a plant specific genomic locus. Current methods for targeted insertion of exogenous DNA typically involve co-transformation of plant tissue with a donor DNA polynucleotide containing at least one transgene and a site specific nuclease (e.g. ZFN) which is designed to bind and cleave a specific genomic locus of an actively transcribed coding sequence.

As used herein the term "zinc fingers," defines regions of amino acid sequence within a DNA binding protein binding domain whose structure is stabilized through coordination of a zinc ion.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference herein in its entirety.

The CRISPR (Clustered Regularly Interspaced Short Palindromic Repeats)/Cas (CRISPR Associated) nuclease system. Briefly, a "CRISPR DNA binding domain" is a short stranded RNA molecule that acting in concert with the CAS enzyme can selectively recognize, bind, and cleave genomic DNA. The CRISPR/Cas system can be engineered to create a double-stranded break (DSB) at a desired target in a genome, and repair of the DSB can be influenced by the use of repair inhibitors to cause an increase in error prone repair. See, e.g., Jinek et al (2012) Science 337, p. 816-821, Jinek et al, (2013), eLife 2:e00471, and David Segal, (2013) eLife 2:e00563).

Zinc finger, CRISPR and TALE binding domains can be "engineered" to bind to a predetermined nucleotide sequence such as a specific site in the CESA1 or CESA3 gene, for example via engineering (altering one or more amino acids) of the recognition helix region of a naturally occurring zinc finger. Yet another possibility is the use of targeted nucleotide editing of DNA using hybrid vertebrate and bacterial immune systems components. Nuclease-deficient type II CRISPR/Cas9 and the activation-induced cytidine deaminase (AID) ortholog PmCDA1 can be engineered to form a synthetic complex (Target-AID) to perform highly efficient target-specific mutagenesis (see Nishida K. et al (2016) *Science*). Similarly, TALEs can be "engineered" to bind to a predetermined nucleotide sequence, for example by engineering of the amino acids involved in DNA binding (the repeat variable di-residue or RVD region). Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "selected" zinc finger protein, CRISPR or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084 and U.S. Publication Nos. 20110301073, 20110239315 and 20119145940.

Additional methods for altering the DNA sequence of specific genes in plants are also known in the art and can be similarly applied to the instant invention. These methods include other forms of mutagenesis, such as ethyl methanesulfonate (EMS)-induced mutagenesis and fast neutron deletion mutagenesis used in a reverse genetics sense (with PCR) to identify plant lines in which the endogenous CESA1 or CESA3 gene has been mutated. For examples of these methods see, Ohshima, et al, (1998) Virology 243: 472-481; Okubara, et al, (1994) Genetics 137:867-874 and Quesada, et al, (2000) Genetics 154:421-436, each of which is herein incorporated by reference. In addition, a fast and automatable method for screening for chemically induced mutations, TILLING (Targeting Induced Local Lesions in Genomes), using denaturing HPLC or selective endonuclease digestion of selected PCR products is also applicable to the instant invention. See, McCallum, et al, (2000) Nat. Biotechnol 18:455-457, herein incorporated by reference.

In yet another embodiment the invention encompasses still additional methods for mutating one or more CESA1 and/or CESA3 alleles. Examples of other methods for altering or mutating a genomic nucleotide sequence in a plant are known in the art and include, but are not limited to, the use of RNA:DNA vectors, RNA:DNA mutational vectors, RNA: DNA repair vectors, mixed-duplex oligonucleotides, self-complementary RNA:DNA oligonucleotides and recombinogenic oligonucleotide bases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference.

In yet another embodiment the invention provides a chimeric gene comprising the following elements:
  a. a plant expressible promoter,
  b. a mutant CESA1 or CESA3 gene encoding a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$, c. a 3' end region comprising transcription termination and polyadenylation signals functioning in cells of a plant.

In yet another embodiment the invention provides a chimeric gene comprising the following elements:
a. a plant expressible promoter,
b. a mutant CESA1 or CESA3 gene encoding a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$, CESA1$^{S1018V}$, CESA1$^{A1023T}$, CESA1$^{L1023T}$ and CESA1$^{V1023T}$,
c. a 3' end region comprising transcription termination and polyadenylation signals functioning in cells of a plant.

A "chimeric gene" or "chimeric construct" is a recombinant nucleic acid sequence in which a promoter or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence. The regulatory nucleic acid sequence of the chimeric gene is not operatively linked to the associated nucleic acid sequence as found in nature.

In the present invention a "plant promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern.

The term "operably linked" as used herein refers to a functional linkage between the promoter sequence and the gene of interest, such that the promoter sequence is able to initiate transcription of the gene of interest.

A "constitutive promoter" refers to a promoter that is transcriptionally active during most, but not necessarily all, phases of growth and development and under most environmental conditions, in at least one cell, tissue or organ.

In yet another embodiment the invention provides a plant comprising a chimeric gene comprising the following elements:
a. a plant expressible promoter,
b. a mutant CESA1 or CESA3 gene encoding a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$,
c. a 3' end region comprising transcription termination and polyadenylation signals functioning in cells of a plant.

In yet another embodiment the invention provides a plant comprising a chimeric gene comprising the following elements:
a. a plant expressible promoter,
b. a mutant CESA1 or CESA3 gene encoding a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{A1018V}$, CESA1$^{S1018V}$, CESA1$^{A1023T}$, CESA1$^{L1023T}$ and CESA1$^{V1023T}$,
c. a 3' end region comprising transcription termination and polyadenylation signals functioning in cells of a plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Moms nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp.,

*Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

In yet another embodiment the invention provides a plant transformation marker system, comprising a herbicide with the structure

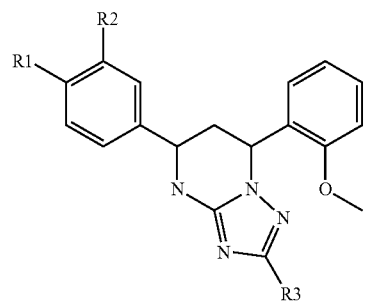

wherein R1 is a halogen, R2 is H or a halogen and R3 is H or —N (CH$_3$)$_2$ and a herbicide resistance gene, which encodes a mutant protein of cellulose synthase subunit 1 (CESA1) or cellulose synthase subunit 3 (CESA3) selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$.

In a specific embodiment the invention provides a plant transformation marker system comprising a herbicide with the structure

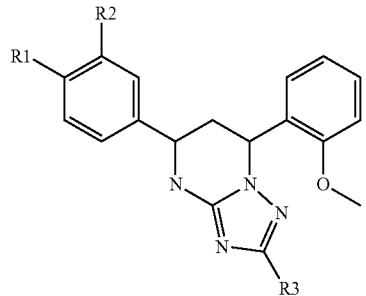

wherein R1 is a Cl, R2 is H or a halogen and R3 is H and a herbicide resistance gene, which encodes a mutant protein of cellulose synthase subunit 1 (CESA1) or cellulose synthase subunit 3 (CESA3) selected from the group consisting of CESA1$^{V297M}$, CESA1$^{S307L}$, CESA1$^{L872F}$, CESA1$^{S82N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$.

In yet another embodiment the invention provides the use of a compound with the following structure

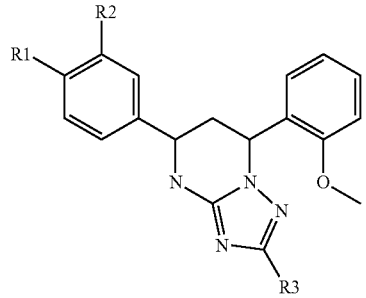

wherein R1 is a halogen, R2 is H or a halogen and R3 is H or —N (CH$_3$)$_2$ as a herbicide.

In yet another embodiment the invention provides the use of a compound with the following structure wherein R1 is a halogen, R2 is H or a halogen and R3 is H or —N (CH$_3$)$_2$ as a herbicide to inhibit cellulose biosynthesis.

In yet another embodiment the invention provides a method to transform plants, said method comprising (1) using a vector comprising a mutant CESA1 or CESA3 gene encoding a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$, and (2) selecting the transformants using a compound as herbicide according to the invention. Preferably, said compound is incorporated in the medium.

It is understood that the vector comprising a mutant CESA1 or CESA3 gene can control the expression of the gene under its own CESA1 or CESA3 promoter or alternatively the CESA1 or CESA3 gene can be brought under control of a heterologous promoter.

In yet another embodiment the invention provides a chimeric gene comprising the following elements:
 a. a plant expressible promoter,
 b. a mutant CESA1 or CESA3 gene encoding a mutant protein selected from the group consisting of CESA1$^{V297M}$, CESA1$^{S307L}$, CESA1$^{L872F}$, CESA1$^{S892N}$, CESA1$^{G892N}$, CESA1$^{K945R}$, CESA1$^{P1010L}$, CESA1$^{G1013R}$, CESA1$^{G1013E}$, CESA1$^{A1018V}$, CESA1$^{S1018V}$, CESA1$^{A1023T}$, CESA1$^{L1023T}$, CESA1$^{V1023T}$, CESA3$^{S983F}$ and CESA3$^{S1037F}$,
 c. a 3' end region comprising transcription termination and polyadenylation signals functioning in cells of a plant.

The following examples are intended to promote a further understanding of the present invention. While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

EXAMPLES

1. C17 Possesses Growth Inhibitory Activity

C17 (5-(4-chlorophenyl)-7-(2-methoxyphenyl)-1,5,6,7-tetrahydro-[1,2,4]triazolo[1,5-a]pyrimidine; ChemDiv, Catalogue #: 7693622), a synthetic molecule, was identified from a chemical screen as a ploidy-inducing compound in *Arabidopsis* protoplasts. To test the effects of C17 on plants, *Arabidopsis* seeds were plated on half MS medium (Murashige, T. and F. Skoog, 1962) in the presence or absence of 200 nM C17 or its analogues. C17-treated plants displayed severe growth inhibition accompanied by radial swelling of the root tip (FIG. 1). Similar but milder defects were observed for wild type plants grown in presence of three C17 analogues (FIG. 1). To dissect the C17 inhibitory effects, we employed confocal laser scanning microscopy (LSM710, ZEISS) to observe the root structure. Five-day-old *Arabidopsis* seedlings grown on vertical plates were transferred to half MS medium containing C17 for further growth. After three-day treatment, the root tips were analysed. Consistent to its growth inhibitory activity, C17 caused cell death at a concentration as little as 25 nM (FIG. 2). At the lowest concentration applied, root cortical cells of the transition zone were affected. This phenotype was aggravated and expanded to other tissues with an increasing dosage of C17 (FIG. 2). In addition to cell death, 100 nM C17 treated plants showed radical rather than polar cell elongation (FIG. 2).

2. Mutations in CESA1 and CESA3 Confer C17 Resistance

To gain insight into growth inhibitory activity of C17, a forward genetic screen was performed to isolate the mutants showing C17 resistance. 300,000 independent ethylmethanesulphonate (EMS) mutagenized seedlings within the Col-0 background were divided into 20 pools and screened for normal root growth in the presence of 2 µM C17. 22 mutants from 12 independent pools were obtained and used to back-cross with WT (Col-0) to define the genetic basis. By analysing the segregation ratio of F2 progenies to C17 sensitivity, 18 mutants were found to exhibited semi-dominant C17 resistance with 1:2:1 ratio (sensitive:intermediate resistant:resistant), whereas 4 mutants (14V, 9R, 9Q and 18A1) exhibited a recessive C17 resistant phenotype with 3:1 ratio (sensitive:resistant), indicating the different mutations were caused by single-gene mutations. Subsequently, all mutants were used to generate mapping populations through crossing with another ecotype (Ler-0). By using 24 general simple sequence length polymorphism (SSLP) markers, these 22 mutants were divided into two groups based on the linkage with SSLP markers, which were designated by corresponding markers, CH4-14494 and CH5-512 respectively. Following fine mapping and genome sequencing approaches to 7L and 2C, a nucleotide mutation at respectively Cellulose Synthase A1 (CESA1) and Cellulose Synthase A3 (CESA3) locus were identified (FIGS. 3A and 3B). Next, the CESA1 and CESA3 loci of the remaining C17 resistant mutants were sequenced. All C17 resistant mutants had a single nucleotide change at CESA1 or CESA3, all resulting into an amino acid change. In total, these mutants contained 10 mutant alleles of CESA1 and 2 of CESA3. Protein sequence analysis showed that the mutated amino acids clustered to the trans-membrane (TM) regions of the CESA proteins (FIG. 3C). Furthermore, amino acid alignment of CESA1/CESA3 homologs from 7 species revealed that 9 mutated amino acids are invariant (FIG. 4). Previous studies reported that CESA1 and CESA3 are two crucial components of cellulose synthase complexes (CSCs) that catalyse the deposition of cellulose, of which the dysfunction results in swollen roots, defective cell elongation, and cell death. Applying C17 to wild type plant mimics these deformities, strengthening the observation that C17 is a cellulose synthase inhibitor.

3. Cell Wall Composition of C17 Resistant Mutants

Given that the amino acid changes in CESA1 and CESA3 of the C17-resistant mutants might cause an altered cell wall, all C17-resistant mutants were used for cell wall composition analysis through Fourier Transform InfraRed (FTIR) spectroscopy. No statistical difference was observed compared to that of wild-type plants, illustrating that in the absence of C17, CESA mutants show a normal cell wall.

4. C17 Operates Differently from the Cellulose Inhibitor Isoxaben

To date, several cellulose synthase inhibitors have been reported. In terms of molecular structure, the C17 compound differs completely from any known cellulose inhibitor. Isoxaben is a typical and potent cellulose synthase inhibitor, for which resistant mutants (ixr1-1, ixr1-2, and ixr2-1) have been described, corresponding to mutant alleles of CESA3 and CESA6. ixr1-1, ixr1-2, and ixr2-1 are still sensitive towards C17 (FIG. 5), illustrating that C17 and isoxaben operate differently.

5. C17 Resistance as a Marker for the Selection of Transformants in *Arabidopsis*

To test whether the identified mutant CESA alleles can be used as an innovative selection marker, using C17 as selective agent, *Arabidopsis* plants were transformed by the floral-dip method using a T-DNA harbouring the $cesa3^{2c}$ mutant allele ($CESA3^{S983F}$) under its own promoter, and a hygromycin selection gene as positive control. To select transgenic plants, seeds resulting from dipped plants were plated on medium supplemented with 2 µM C17. Out of a total of 2,000 plants, 5 plants could be identified showing normal root growth (FIG. 6), similar to the frequency seen upon selection on hygromycin-containing medium. PCR analysis confirmed these plants to harbour the T-DNA construct.

6. C17-Induced Depletion of Membrane CESAs Results in a Weaker Cell Wall

We observed that C17 treatment resulted in the depletion of the CESA complex from the plasma membrane of wild-type root cells with a dramatic drop after 10 to 15 min of C17 application. Because the cellulose synthesized by the CESA1/CESA3 complex is a primary cell wall component, it was expected that C17-treated plants would display a weaker cell wall, which can be visualized by the uptake of propidium iodide (PI) following the application of a gentle pressure on the root. Indeed, cell wall weakening was observed in the root elongation zone within 2 h after applying C17, which increased over time and correlated with growth inhibition. No PI-positive cells and growth inhibition were observed in C17-tolerant mutants.

Materials and Methods

1. Analysis of Root Growth and Observation of Root Structure

For studying the growth inhibitory effects of C17 on plants, wild type and C17 resistant mutants were germinated on half MS medium (Murashige and Skoog, 1962) supplemented with or without indicated levels of C17 or its analogs. Seven-day-old seedlings were photographed. For observation of the root structure, five-day-old *Arabidopsis* seedlings were transferred to half MS medium containing different dosages of C17. After a three-day treatment, seedlings were photographed and their root tips were stained with propidium iodide (PI), a fluorescent dye that is excluded from the membranes of healthy cells but penetrates the plasma membrane of dead cells. The stained root tips were visualized by confocal laser scanning microscopy (LSM710, ZEISS). The ixr1-1 (collection number CS6201), ixr1-2 (CS6202) and ixr2-1 (CS6203) mutants were acquired from the ABRC. Five-day-old *Arabidopsis* seedlings were transferred to half MS medium with or without 200 nM C17. After 3 day, the plants were photographed.

2. C17 Resistant Mutants Screening

To obtain mutants resistant to C17, seeds from an ethylmethanesulphonate (EMS)-treated seed collection with Col background were plated on half MS medium containing 2 µM C17. After growing for 7 days under long-day conditions (16 h of light/8 h of darkness) at 22° C., plants with a long root were identified as C17 resistant mutants. Out of a total of 300,000 independent EMS mutagenized seeds (divided over 20 pools) 22 mutants were isolated (from 12 independent pools).

3. Map-Based Cloning

To define the mutations underlying C17 resistance, all C17 resistant mutants were backcrossed with wild-type (Col-0) plants to obtain F1 progenies. F2 progenies from self-pollinated F1 plants were grown in the presence of 500 nM C17 for 7 days, allowing calculation of the segregation ratio of C17 resistance within the F2 progenies. All mutants were also used to generate mapping populations through crossing with another ecotype (Ler-0). Simple sequence length polymorphism (SSLP) markers (Table 1) were used to map the position of the mutated genes in *Arabidopsis* genome. Subsequently, the mutant genes were identified through candidate gene sequencing.

4. Proteins Alignment

Protein amino acid sequences of CESA1 and CESA3 from 7 species, extracted from the GenBank database, were aligned using CLUSTALW. Sequence data can be found under the following accession numbers: $CESA1_{A.thaliana}$ (NP_194967), $CESA1_{G.max}$ (XP_003522623), $CESA1_{F.vesca}$ (XP_004291468), $CESA1_{V.vinifera}$ (XP_002282575), $CESA1_{S.lycopersicum}$ (XP_004245031), $CESA1_{Z.mays}$ (NP_001104954), $CESA1_{O.sativa}$ (NP_001054788), $CESA3_{A.thaliana}$ (NP_196136), $CESA3_{G.max}$ (XP_003540527), $CESA3_{F.vesca}$ (XP_004306536), $CESA3_{V.vinifera}$ (XP_002278997), $CESA3_{S.lycopersicum}$ (XP_004229630), $CESA3_{Z.mays}$ (NP_001105621), and $CESA3_{O.sativa}$ (NP_001059162).

5. Plant Transformations $CESA3^{2C}$ sequences were amplified from cDNA of $CESA3^{2C}$ mutant plants by PCR using the following primer pairs (CESA3_ATTB1: GGGGACAAGTTTGTACAAAAAAGCAGGCTTCA TGGAATCCGAAGGAGAAACCGCG (SEQ ID NO: 1); CESA3_ATTB2: GGGGACCACTTT GTACAAGAAAGCTGGGTGTCGCTTCTCAACAGTTGATTCC SEQ ID NO: 2). The resulting fragments were created with the Pfu DNA polymerase kit (Promega) and were cloned into a pDONR221 entry vector by BP recombination cloning and subsequently transferred into the modified pGWB2 destination vector in which 35S promoter was replace by CESA3 promoter. *Arabidopsis* plants (cesa3$^{je5}$) were transformed using the floral-dip method as described (Clough and Bent, 1998). T1 seeds were germinated on MS medium supplemented with 2 µM C17 or 25 mg/l hygromycin to screen for transformants.

6. Detection of Cell Wall Weakening

For the detection of cell wall weakening, 3-day-old seedlings grown on half-strength MS medium were transferred to liquid medium without or with 200 nM C17. The root tips were stained with 10 mg mL$^{-1}$ prodium iodide for three min. The stained root tips were put on the Nunc™ Lab-Tek™ Chambered Coverglass (Catalog #155361) without pressure or microscope slide with cover slip that gave a gentle exerting of pressure. By using confocal laser scanning microscopy (LSM710, ZEISS), the brittle cells could be visualized by the uptake of PI.

REFERENCES

Austin, R. S., Vidaurre, D., Stamatiou, G., Breit, R., Provart, N. J., Bonetta, D., Zhang, J., Fung, P., Gong, Y., Wang, P. W., McCourt, P., and Guttman, D. S. 2011. Next-generation mapping of *Arabidopsis* genes. Plant J 67, 715-725.

Brabham, C and DeBolt, S. 2013. Chemical genetics to examine cellulose biosynthesis. Frontiers in Plant science 3, article 309.

Clough, S. J. and Bent A. F. 1998. Floral dip: a simplified method for *Agrobacterium*-mediated transformation of *Arabidopsis thaliana*. Plant J 16, 735-743.

Deprez, T., Vernhettes, S., Fagard, M., Refregier, G., Desnos, T., Aletti, E., Py, S and Höfte, H. 2002. Resistance against herbicide Isoxaben and cellulose deficiency caused by distinct mutations in same cellulose synthase isoform CESA6. Plant Physiol. 128, 482-490.

Endler, A. and Persson, S. 2011. Cellulose synthases and synthesis in *Arabidopsis*. Mol. Plant 4, 199-211.

Festucci-Buselli, R. A., Otoni, W. C. and Joshi, C. P. 2007. Structure, organization and functions of cellulose synthase complexes in higher plants. Braz. J. Plant. Physiol. 19, 1-13.

Garcia-Angulo, P., Alonso-Simon, A., Encina, A., Alvarez, J. M., and Acebes, J. L. 2012. Cellulose biosynthesis inhibitors: comparative effect on bean cell cultures. Int J Mol Sci 13, 3685-3702.

Harris, D. M., Corbin, K., Wang, T., Gutierrez, R., Bertolo, A. L., Petti, C., Smilgies, D. M., Estevez, J. M., Bonetta, D., Urbanowicz, B. R., Ehrhardt, D. W., Somerville, C. R., Rose, J. K., Hong, M., and Debolt, S. 2012. Cellulose microfibril crystallinity is reduced by mutating C-terminal transmembrane region residues CESA1$^{A903V}$ and CESA3$^{T942I}$ of cellulose synthase. Proc Natl Acad Sci USA 109, 4098-4103.

Heim, D. R., Roberts, J. L., Pike, P. D. and Larrinua, I. M. 1989. Mutations of a locus of *Arabidopsis thaliana* confers resistance to the herbicide isoxaben. Plant Physiol. 90, 146-150

Kimura, S., Laosinchai, W., Itoh, T., Cui, X., Linder, R. and Brwon, R. M. Jr. 1999. Immunogold labeling of rosette terminal cellulose synthesizing complexes in the vascular plant *Vigna angularis*. The Plant Cell 11, 2075-2085.

Lei, L., Li, S. and Gu, Y. 2012. Cellulose synthase complexes: composition and regulation. Frontiers in plant science, 3, article 75.

Murashige. T, and F. Skoog. 1962. A revised medium for rapid growth and bioassays with tobacco cultures. Physiol. Plant 15, 473-497.

Scheible, W. R., Eshed, R., Richmond, T., Delmer, D. and Somerville, C. 2001. Modifications of cellulose synthase confer resistance to isoxaben and thiazolidinone herbicides in Arabidospsis Ixr1 mutants. Proc. Nat. Acad. Sci. USA 98, 10079-10084.

---

The invention claimed is:

1. A non-naturally occurring plant mutant CESA1 protein selected from the group consisting of:

(a1) the mutant CESA1 protein having mutation of valine residue to methionine residue at the amino acid sequence position 297 of the wild-type CESA1 plant protein as set forth in GenBank database sequence accession number: NP_194967 which corresponds to the amino acid sequence position 27 of SEQ ID NO: 3, (a2) the mutant CESA1 protein having mutation of valine residue to methionine residue at the amino acid sequence position 301 of the wild-type CESA1 plant protein as set forth in GenBank database sequence accession number: XP_003522623 which corresponds to the amino acid sequence position 27 of SEQ ID NO: 3, (a3) the mutant CESA1 protein having mutation of valine residue to methionine residue at the amino acid sequence position 285 of the wild-type CESA1 plant protein as set forth in GenBank database sequence accession number: XP_004291468.1 which corresponds to the amino acid sequence position 27 of SEQ ID NO: 3, (a4) the mutant CESA1 protein having mutation of valine residue to methionine residue at the amino acid sequence position 441 of the wild-type CESA1 plant protein as set forth in GenBank database sequence accession number: XP_002282575.2 which corresponds to the amino acid sequence position 27 of SEQ ID NO: 3,
(a5) the mutant CESA1 protein having mutation of valine residue to methionine residue at the amino acid sequence position 301 of the wild-type CESA1 plant protein as set forth in GenBank database sequence accession number: XP_004245031 which corresponds to the amino acid sequence position 27 of SEQ ID NO: 3,
(a6) the mutant CESA1 protein having mutation of valine residue to methionine residue at the amino acid sequence position 293 of the wild-type CESA1 plant protein as set forth in GenBank database sequence accession number: NP_001104954 which corresponds to the amino acid sequence position 27 of SEQ ID NO: 3,
(a7) the mutant CESA1 protein having mutation of valine residue to methionine residue at the amino acid sequence position 294 of the wild-type CESA1 plant protein as set forth in GenBank database sequence accession number: NP_001054788.1 which corresponds to the amino acid sequence position 27 of SEQ ID NO: 3,
(a8) the mutant CESA1 protein having mutation of leucine residue to phenylalanine residue at the amino acid sequence position 872 of the wild-type CESA1 plant protein as set forth in GenBank database sequence accession number: NP_194967 which corresponds to the amino acid sequence position 62 of SEQ ID NO: 3,
(a9) the mutant CESA1 protein having mutation of leucine residue to phenylalanine residue at the amino acid sequence position 876 of the wild-type CESA1 plant protein as set forth in GenBank database sequence accession number: XP_003522623 which corresponds to the amino acid sequence position 62 of SEQ ID NO: 3,
(a10) the mutant CESA1 protein having mutation of leucine residue to phenylalanine residue at the amino acid sequence position 860 of the wild-type CESA1 plant protein as set forth in GenBank database sequence accession number: XP_004291468.1 which corresponds to the amino acid sequence position 62 of SEQ ID NO: 3,
(a11) the mutant CESA1 protein having mutation of leucine residue to phenylalanine residue at the amino acid sequence position 1016 of the wild-type CESA1 plant protein as set forth in GenBank database sequence accession number: XP_002282575.2 which corresponds to the amino acid sequence position 62 of SEQ ID NO: 3,
(a12) the mutant CESA1 protein having mutation of leucine residue to phenylalanine residue at the amino acid sequence position 877 of the wild-type CESA1 plant protein as set forth in GenBank database sequence accession number: XP_004245031 which corresponds to the amino acid sequence position 62 of SEQ ID NO: 3;
(a13) the mutant CESA1 protein having mutation of leucine residue to phenylalanine residue at the amino acid sequence position 866 of the wild-type CESA1 plant protein as set forth in GenBank database sequence accession number: NP_001104954 which corresponds to the amino acid sequence position 62 of SEQ ID NO: 3,
(a14) the mutant CESA1 protein having mutation of leucine residue to phenylalanine residue at the amino acid sequence position 867 of the wild-type CESA1 plant protein as set forth in GenBank database sequence accession number: NP_001054788.1 which corresponds to the amino acid sequence position 62 of SEQ ID NO: 3,
(a15) the mutant CESA1 protein having mutation of serine residue to asparagine residue at the amino acid sequence position 892 of the wild-type CESA1 plant protein as set forth in GenBank database sequence accession number: NP_194967 which corresponds to the amino acid sequence position 82 of SEQ ID NO: 3,
(a16) the mutant CESA1 protein having mutation of serine residue to asparagine residue at the amino acid sequence position 896 of the wild-type CESA1 plant protein as set forth in GenBank database sequence accession number: XP_003522623 which corresponds to the amino acid sequence position 82 of SEQ ID NO: 3,
(a17) the mutant CESA1 protein having mutation of serine residue to asparagine residue at the amino acid sequence position 880 of the wild-type CESA1 plant protein as set forth in GenBank database sequence accession number: XP_004291468.1 which corresponds to the amino acid sequence position 82 of SEQ ID NO: 3,
(a18) the mutant CESA1 protein having mutation of serine residue to asparagine residue at the amino acid sequence position 1036 of the wild-type CESA1 plant protein as set forth in GenBank database sequence accession number: XP_002282575.2 which corresponds to the amino acid sequence position 82 of SEQ ID NO: 3,
(a19) the mutant CESA1 protein having mutation of alanine residue to valine residue at the amino acid sequence position 1018 of the wild-type CESA1 plant protein as set forth in GenBank database sequence accession number: NP_194967 which corresponds to the amino acid sequence position 208 of SEQ ID NO: 3,
(a20) the mutant CESA1 protein having mutation of alanine residue to valine residue at the amino acid sequence position 1022 of the wild-type CESA1 plant protein as set forth in GenBank database sequence accession number: XP_003522623 which corresponds to the amino acid sequence position 208 of SEQ ID NO: 3,
(a21) the mutant CESA1 protein having mutation of alanine residue to valine residue at the amino acid sequence position 1006 of the wild-type CESA1 plant protein as set forth in GenBank database sequence accession number: XP_004291468.1 which corresponds to the amino acid sequence position 208 of SEQ ID NO: 3,
(a22) the mutant CESA1 protein having mutation of alanine residue to valine residue at the amino acid sequence position 1162 of the wild-type CESA1 plant protein as set forth in GenBank database sequence accession number: XP_002282575.2 which corresponds to the amino acid sequence position 208 of SEQ ID NO: 3,
(a23) the mutant CESA1 protein having mutation of alanine residue to valine residue at the amino acid sequence position 1023 of the wild-type CESA1 plant protein as set forth in GenBank database sequence accession number: XP_004245031 which corresponds to the amino acid sequence position 208 of SEQ ID NO: 3,
(a24) the mutant CESA1 protein having mutation of alanine residue to threonine residue at the amino acid sequence position 1023 of the wild-type CESA1 plant protein as set forth in GenBank sequence database sequence accession number: NP_194967 which corresponds to the amino acid sequence position 213 of SEQ ID NO: 3,
(a25) the mutant CESA1 protein having mutation of alanine residue to threonine residue at the amino acid sequence position 1027 of the wild-type CESA1 plant protein as set forth in GenBank database sequence accession number: XP_003522623 which corresponds to the amino acid sequence position 213 of SEQ ID NO: 3, and
(a26) the mutant CESA1 protein having mutation of alanine residue to threonine residue at the amino acid sequence position 1011 of the wild-type CESA1 plant protein as set forth in GenBank database sequence accession number: XP_004291468.1 which corresponds to the amino acid sequence position 213 of SEQ ID NO: 3;

and wherein a transgenic plant overexpressing said non-naturally occurring plant mutant CESA1 protein exhibits tolerance to C17 herbicide, and sensitivity to flupoxam, isoxaben and indaziflam herbicides as compared to a control or wild-type plant of the same plant species lacking expression of said non-naturally occurring plant mutant CESA1 protein, and grown under identical growth conditions.

2. A gene comprising the following elements:
a plant expressible promoter which is operably linked to a nucleic acid encoding the non-naturally occurring plant mutant CESA1 protein of claim 1, and wherein said promoter is heterologous to said nucleic acid; and
a 3' end region comprising transcription termination and polyadenylation signals functioning in cells of a plant.

3. A transgenic plant transformed with the gene of claim 2.

4. A method of treating a plant, the method comprising:
treating the plant with a compound having following structure:

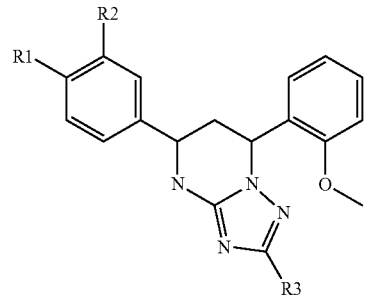

wherein R1 is a halogen, R2 is H or a halogen and R3 is H or —N(CH$_3$)$_2$; wherein the plant is transformed with a DNA construct comprising the gene of claim 2, and wherein said non-naturally occurring plant mutant CESA1 protein is overexpressed in said transformed plant.

5. The method according to claim 4, wherein the compound is an inhibitor of cellulose synthesis.

6. The method according to claim 4, wherein R1 is Cl, R2 is H and R3 is H.

* * * * *